US005782866A

United States Patent [19]
Wenstrom, Jr.

[11] Patent Number: 5,782,866
[45] Date of Patent: Jul. 21, 1998

[54] SYSTEM FOR ANCHORING TISSUE TO BONE

[75] Inventor: Richard F. Wenstrom, Jr., Norwood, Mass.

[73] Assignee: Ethicon, Inc., Somerville, N.J.

[21] Appl. No.: 823,826

[22] Filed: Mar. 25, 1997

[51] Int. Cl.$^6$ .................................................. A61B 17/04
[52] U.S. Cl. ........................... 606/232; 606/72; 606/75; 606/78
[58] Field of Search ................... 606/232, 72–75

[56] References Cited

U.S. PATENT DOCUMENTS

| | | | |
|---|---|---|---|
| 3,910,281 | 10/1975 | Kletschka et al. | 606/232 |
| 4,750,492 | 6/1988 | Jacobs | 606/232 |
| 4,898,156 | 2/1990 | Gatturna et al. | 606/72 |
| 4,946,468 | 8/1990 | Li | 606/232 |
| 5,100,417 | 3/1992 | Cerier et al. | 606/139 |
| 5,156,616 | 10/1992 | Meadows et al. | 606/232 |
| 5,522,844 | 6/1996 | Johnson | 606/232 |

*Primary Examiner*—Gary Jackson
*Attorney, Agent, or Firm*—Nutter, McClennen & Fish, LLP

[57] ABSTRACT

A system for anchoring tissue to bone includes an anchor member having an outer, bone engaging wall, a distal end, and a proximal end, a suture receiving slot extending partially into the anchor member, forming an internal passageway ending in a suture seat. The suture seat is integral with the anchor member and is formed within the anchor member.

27 Claims, 2 Drawing Sheets

SYSTEM FOR ANCHORING TISSUE TO BONE

CROSS-REFERENCE TO RELATED APPLICATIONS

Not Applicable.

STATEMENT REGARDING FEDERALLY SPONSORED RESEARCH

Not Applicable.

FIELD OF THE INVENTION

The invention relates to a system for anchoring tissue to bone, and more particularly to a system for anchoring soft tissue to bone.

BACKGROUND OF THE INVENTION

Systems and devices for anchoring sutures to bone are commonly used in medical or surgical operations. Anchored sutures are typically used to attach soft tissue, such as ligaments, tendons and muscles, to bone or inanimate objects, such as prostheses, to bone. The attachment may hold the tissue to a bone for an extended period of time to allow healing to occur. Alternatively, the attachment may be used to hold tissue in place temporarily during a surgical procedure to help perform or optimize that procedure.

Conventional suture anchors may be inserted into a preformed bore in the bone, driven directly into the bone or driven into the bone in the manner of a common screw, the screw-type anchor being inserted with or without a preformed bore in the bone. U.S. Pat. No. 4,898,156 provides an example of the insertion-type suture anchor. In this example, a suture is attached to the anchor by capturing a knotted end of the suture in the anchor's distally located blind hole, while the free end of the suture exits the anchor by a side slot or an axial through-hole in the anchor body.

An example of the screw-type suture anchor is provided in U.S. Pat. No. 5,156,616. A suture is attached to this anchor by capturing a knotted end of the suture thread in a distal portion of an axial passageway, with the free end of the suture extending proximally through the axial passageway.

Conventional suture anchors for attaching soft tissue to bone often require that a knot be tied in the suture thread in order to attach the suture to the anchor. Such knot tying procedures can be quite difficult and time consuming, especially in closed (e.g. arthroscopic) surgical procedures. It is sometimes desirable to avoid knots and other bulky attachment means because such attachments can irritate tissue in the area in which they are located, and can become loose over time.

Some conventional suture anchors suffer from additional disadvantages as well. Many conventional suture anchors have sharp edges or provide small passageways through which the suture must be threaded, causing difficulties or delays in threading the suture. In some instances, off-axis suture seating or off-axis exit features found on conventional anchors may result in disadvantageous movement or twisting of the anchor after insertion in the bone. Attachment of the suture thread to a distal portion of the anchor may lead to the same disadvantageous movement or twisting.

Moreover, where two free ends of suture thread are required or desired, unwanted tangling and knotting may occur when two suture ends exit the anchor through a single hole in the anchor body or on the same side of the anchor body.

One disadvantage to using screw-type anchor devices is that suture thread can be abraded or otherwise damaged when the anchor is threaded into bone as the suture is disposed between the bone and threads of the anchor. It is thus necessary to drill a hole of larger than desired diameter in the bone in order to prevent any such damage to the suture when the suture anchor is deployed.

SUMMARY OF THE INVENTION

The present invention provides a system for anchoring tissue to bone including an anchor member having a suture receiving slot.

In one embodiment, the suture receiving slot is formed in a sidewall of the anchor member. The slot extends from an opening in the sidewall to an internal suture seat, creating a passageway by which an intermediate portion of suture thread may be threaded. The anchor member can also include one or more suture retaining structures which serve to retain a captured portion of suture thread within the suture receiving slot.

In another embodiment, the anchor member is substantially cylindrical and includes external threads located on its outer surface. The suture receiving slot is formed in the distal end of the anchor member and extends proximally to an internal retaining wall. The anchor member also includes one or more breaks in the external threads. The breaks are aligned with the suture receiving slot and may be used to seat a portion of the suture thread extending proximally from the internal retaining wall.

BRIEF DESCRIPTION OF THE DRAWINGS

The invention will be more fully understood by reference to the following detailed description when considered in conjunction with the accompanying drawings, in which:

FIGS. 3–6 illustrate additional embodiments of a suture receiving slot of the anchor member of FIG. 2.

DETAILED DESCRIPTION OF THE INVENTION

Figure 1:
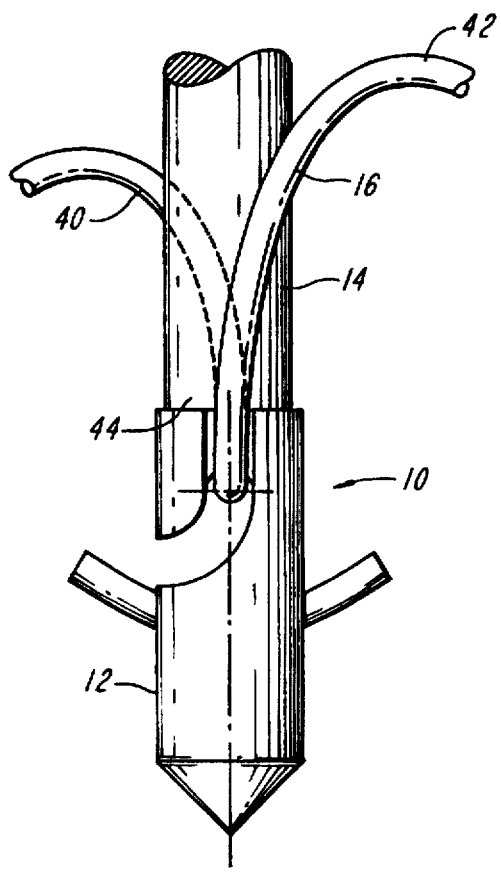
FIG. 1 is an elevated view of an embodiment of the system for anchoring soft tissue of the invention.

A system 10 for anchoring tissue to bone is illustrated in FIG. 1. This exemplary system includes an anchor member 12, an installation tool 14, and a suture thread 16.

Figure 2:
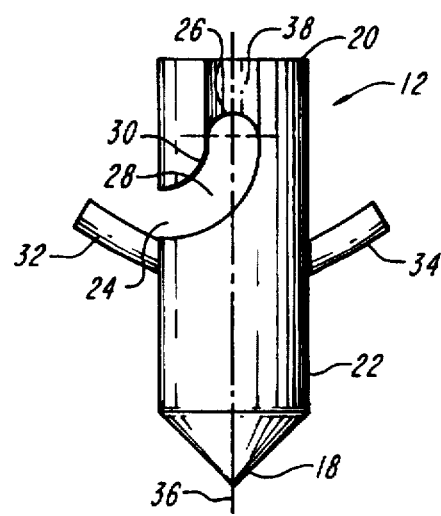
FIG. 2 is an elevated view of an anchor member of a first embodiment of the invention.

Referring now to FIG. 2, an anchor member 12 in accordance with the invention is illustrated. The anchor member 12 has a distal end 18, a proximal end 20, a sidewall 22 disposed between the distal and proximal ends, and a suture receiving slot 24. The suture receiving slot 24 extends from an opening formed in the side wall 22 of the anchor member 12 to a suture seat 26 within the anchor member 12. The suture receiving slot 24 forms an internal passageway 28 and includes one or more suture retaining structures 30. The slotted anchor member may be made using any biomedically compatible material. Titanium alloys are preferred, but absorbable and non-absorbable polymers may also be employed.

In the embodiment of FIG. 2, the anchor member 12 is substantially cylindrical in shape and the distal end 18 forms an apex. The exemplary anchor member 12 additionally comprises two opposed deformable barbs 32, 34 extending from the side wall 22 of the anchor member 12. As further shown in FIG. 2, the free ends of the deformable barbs 32, 34 may extend outward from the anchor member 12 and proximally (toward the proximal end 20 of the anchor member 12) such that each barb defines an angle that is between about 10º and 90º with respect to a longitudinal axis 36 of the anchor member 12. More or fewer deformable barbs may be provided as desired to ensure proper retention of the anchor member 10 within a bone. In an alternative embodiment, the anchor member may include external threads as a structural element by which the anchor member is secured within a bone.

In the exemplary anchor member 12, the suture receiving slot 24 is curvilinear. The suture receiving slot 24 extends from an opening in the sidewall 22 of the substantially cylindrical anchor member 12, and forms a passageway 28 which extends inward to the longitudinal axis 36 of the anchor member 12 as it curves toward the proximal end 20 of the anchor member 12. Accordingly, one interior end of the passageway 28 forms a suture seat 26 which is transverse to the longitudinal axis 36 of the anchor member 12, and opposed to the proximal end 20 of the anchor member 12. If the anchor member 12 is solid, the suture seat 26 will be a wall interior to, and integral with, the anchor member 12 which marks an end of the passageway 28. If the anchor member 12 is not solid, the suture seat 26 may be formed by the surfaces integral with the sidewall 22 of the anchor member 12 which mark an end of the passageway 28.

The suture seat 26, as shown in FIG. 2, is coaxial with the longitudinal axis 36. This configuration, wherein the suture seat 26 and the suture retaining structures 30 are adapted to retain a suture thread so that the thread is coaxial with the longitudinal axis 36, may be referred to as "on-axis" suture retention. As required, off-axis suture retention configurations, wherein the retained suture is not coaxial with the longitudinal axis 36, may also be employed.

The exemplary suture seat 26 is located toward the proximal end 20 of the anchor member 12. Preferably, suture seat 26 is disposed proximally to the deformable barbs 32, 34. While proximal suture seating may be advantageous, other locations may be used as required.

The suture seat 26 and suture retaining structures 30 may be provided with rounded edges. Rounding the edges will reduce the likelihood of damaging a suture thread during threading or use of the system. The anchor member 12 may also be provided with grooves 38, extending from the suture seat 26 to the proximal end 20 of the anchor member, capable of seating a length of suture thread.

The anchor member 12 is further provided with one or more suture retaining structures 30. The term "suture retaining structure," as used herein, refers to any structural element which serves to retain a suture in the suture seat 26 or which reduces the probability that a retained suture will escape from the suture receiving slot 24 when the retained suture is slack.

Where the passageway 28 is non-linear, the suture retaining structure may comprise an obstruction formed in the sidewall 22 of the anchor member 12 by a change in direction of the passageway 28. In the exemplary embodiment shown in FIG. 2, the suture retaining structure 30 is formed in the sidewall 22 of the anchor member 12 by the curvilinear shape of the passageway 28.

Figure 4:
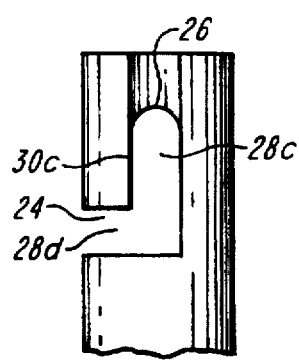
Figure 5:
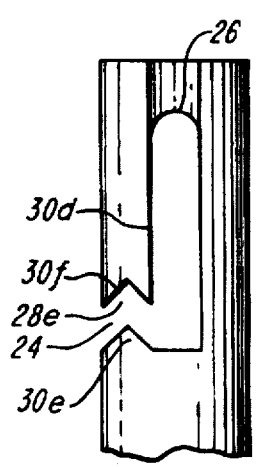

Additional embodiments in which suture receiving slots 24 form multidirectional passageways are shown in FIGS. 3–5. In each of these embodiments, changes in the direction of the passageways 28 create obstructions which serve as suture retaining structures 30a–g.

Figure 6:
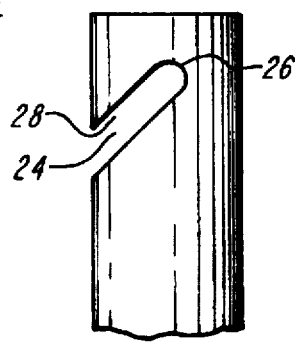

In FIGS. 3–4, the suture receiving slots 24 each define linear passageway segments 28a–d which communicate at right angles. Each of these slots has a first linear passageway segment 28a, 28c which is parallel to the longitudinal axis 36 of the anchor member 12, and a second linear passageway segment 28b, 28d which is perpendicular to and communicates with the first linear passageway segment. The suture receiving slot 24 illustrated in FIG. 5 is similar to that of FIG. 4, but additional suture retaining structures 30e, 30f are provided in the transverse passageway segment 28e. In FIG. 6, a suture receiving slot 24 which defines a linear passageway 28 is illustrated.

Referring again to FIG. 1, the tissue-to-bone anchoring system of the invention may also comprise a suture thread 16, having an intermediate portion and two free ends 40, 42, engaged within the suture receiving slot 24 such that the intermediate portion of the suture thread 16 is retained within the suture receiving slot 24 by the suture retaining structures 30 and the suture seat 26. The two free ends 40, 42 of the suture thread 16, that is, the portions of the suture thread 16 which are not engaged within the suture receiving slot, may then extend toward the proximal end 20 of the anchor member 12 from opposing sides of the suture receiving slot 24. Additionally, a portion of the suture thread 16 may be seated in grooves 38 formed in the anchor member 12.

The system for anchoring soft tissue to bone of the present invention may also comprise an anchor member insertion tool 14 having a handle end (not shown) and a distal end 44 as shown in FIG. 1. The distal end 44 of the tool 14 may be matable with the proximal end 20 of the anchor member 12. The anchor member 12 may then be removably pre-mated to the distal end 44 of the insertion tool 14.

Figure 7:
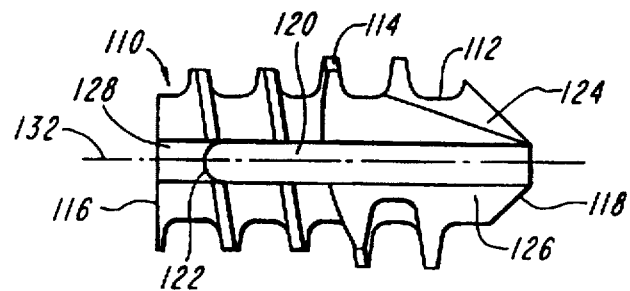
FIG. 7 is an elevated view of an anchor member of a second embodiment of the invention.
Figure 8:
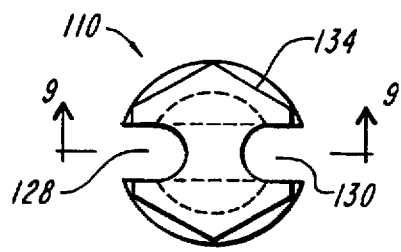
FIG. 8 illustrates an axial view of the anchor member of FIG. 7.
Figure 9:
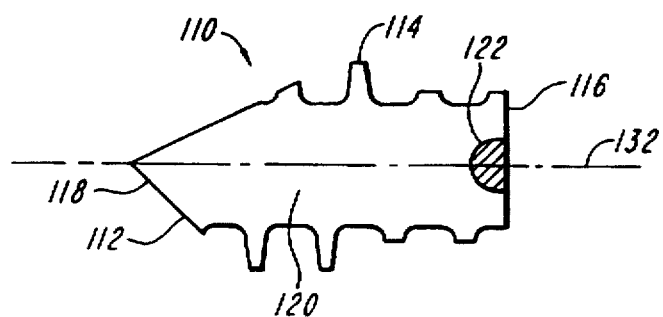
FIG. 9 is a cross section of the anchor member of FIG. 8 taken along line 9—9.

FIGS. 7 to 9 are illustrative of an alternative embodiment of an anchor member 110 useful with the system of the invention. A substantially cylindrical anchor member 110 is provided. The anchor member has an outer, or bone engaging, wall 112 with external threads 114 formed on at least a portion of the outer wall. The anchor member 110 also has a proximal end 116 and a distal end 118, the distal end forming an apex.

A suture receiving slot 120 is formed in the distal end 118 of the anchor member 110. The suture receiving slot 120 extends from an opening at the distal end 118 of the anchor member to an internal retaining wall 122 within the anchor member 110. The slot 120 separates at least a portion of the distal end of the anchor member into two adjacent segments 124, 126.

The anchor member 110 is further provided with at least one break 128 formed in the external threads 114 of the anchor member. The exemplary anchor member 110 is provided with twin opposed breaks 128, 130 in the external threads 114. The breaks 128, 130, as best illustrated in FIG. 8, are preferably made in each thread over the length of the anchor member and they are effective to seat a length of suture thread within the threads. That is, the breaks 128, 130, which are preferably aligned with the suture receiving slot 120, extend from the suture receiving slot 120 to the proximal end 116 of the anchor member 110. An elongate slot or groove (as shown in FIGS. 7 and 8, grooves accompany each of the breaks 128, 130 in the threads) may also be formed in the outer wall 112 coincident with the breaks in the threads, allowing the suture thread to be seated more deeply within the threads.

The suture receiving slot, as well as the twin opposed breaks in the external threads of the anchor member, may be coaxial with a longitudinal axis 132 of the anchor member 110. Accordingly, the slotted anchor member may be adapted so that the retained suture is centered on the longitudinal axis 132 of the anchor member ("on-axis" suture retention). As with the embodiment of the anchor member shown in FIGS. 1–6, off-axis suture retention may be employed as required.

The suture receiving slot 120 may also be adapted to seat a portion of suture thread in proximity to the proximal end 116 of the anchor member 110. In one embodiment this can be accomplished by extending the slot over at least one-half of the length of the anchor member.

Anchor member 110 may be part of a system for anchoring tissue to bone. This system may also comprise a length of suture thread (not shown) disposed in the suture receiving slot 120 such that an intermediate portion of the thread is retained within the anchor member 110 by the internal retaining wall 122. The two free ends of the suture thread may then extend proximally across the length of the anchor member and be disposed within the breaks 128 in the external threads 114 formed on opposite sides of the anchor member 110.

The width of the suture receiving slot 120 must be sufficient to receive and retain the suture thread and will depend upon the overall dimensions of the anchor member. The width of the suture receiving slot 120 is not otherwise particularly limited, but by way of example, can be in the range of about 0.010 to 0.036 inches. Similarly, the breaks 128, 130 in the external threads 114 must be of sufficient width and depth to retain the suture thread within the length of the breaks. The width of the breaks 128, 130 in the external threads 114 is not otherwise particularly limited, but by way of example, can be in the range of about 0.010 to 0.036 inches. The breaks in the threads can be of virtually any depth as long as they are not so deep as to compromise the structural integrity of the anchor member. Preferably, the width of the remaining anchor material (between the opposed breaks) should be in the range of about 0.020 to 0.048 inches.

The slotted anchor member 110 of the invention may be adapted, by appropriate configuration of the external threads 114 and the breaks 128, 130 therein, to seat within a bore formed in a bone wherein the bore has a diameter that is substantially equal to or slightly less than the diameter of the anchor member 110.

The system for anchoring soft tissue to bone using anchor member 110 may also comprise an anchor member installation tool 14 having a distal end 44 which is adapted to mate with the proximal end 116 of the anchor member 110. In one embodiment, as shown in FIG. 8, the external threads 114 closest to the proximal end 116 of the exemplary anchor member 110 can be adapted to form a hexagonal region 134 which extends from a predetermined point along the longitudinal axis 132 to the proximal end 116 of the anchor member 110. The hexagonal region 134 may be used to engage or mate with an installation tool 14. In some embodiments, the anchor member 112 may be removably pre-mated to the distal end 44 of the insertion tool 14.

It will be understood that the foregoing is only illustrative of the principles of the invention, and that various modifications can be made by those skilled in the art without departing form the scope and spirit of the invention. All references cited herein are expressly incorporated by reference in their entirety.

What is claimed is:

1. A system for anchoring tissue to bone, comprising:
an anchor member adapted to be retained in bone, having a distal end, a proximal end, a sidewall disposed between the distal and proximal ends, a suture seat formed in the interior of the anchor member, and a suture receiving slot defined in and originating in the side wall and extending to the suture seat.

2. The system of claim 1, wherein the anchor member further has at least one suture retaining structure.

3. The system of claim 2, wherein the at least one suture retaining structure is integral with the suture receiving slot.

4. The system of claim 3, wherein the at least one suture retaining structure has rounded edges.

5. The system of claim 3, wherein the suture receiving slot defines a passageway between the suture seat and the exterior of the anchor member.

6. The system of claim 5, wherein the passageway is non-linear.

7. The system of claim 6, wherein the passageway is curvilinear.

8. The system of claim 6, wherein the passageway comprises two linear passageway segments which communicate at a right angle.

9. The system of claim 6, wherein the at least one suture retaining structure comprises an obstruction formed in the sidewall of the anchor member and created by a change in direction of the passageway.

10. The system of claim 3, wherein the anchor member further has a longitudinal axis, the anchor member is substantially cylindrical, and the distal end forms an apex.

11. The system of claim 10, further comprising at least one deformable barb extending from the sidewall of the anchor member.

12. The system of claim 11, having two opposed barbs, the free end of each barb extending away from the anchor member and toward the proximal end, each barb defining an angle that is between about 10° and 90° with the longitudinal axis of the anchor member.

13. The system of claim 10, wherein the suture seat and the at least one suture retaining structure are adapted to seat a suture thread along the longitudinal axis of the anchor member.

14. The system of claim 3, further comprising a suture thread having an intermediate portion and two free ends, the intermediate portion of the suture thread being engaged within the suture receiving slot, and the two free ends extending past the proximal end of the anchor member.

15. The system of claim 3, further comprising an anchor member insertion tool having a handle end and a distal end, the distal end being matable with the proximal end of the anchor member.

16. The system of claim 15, wherein the anchor member is removably pre-mated to the distal end of the insertion tool.

17. A system for anchoring tissue to bone, comprising:
a substantially cylindrical anchor member having a longitudinal axis, a distal end, a proximal end, a side wall disposed between the distal and proximal ends, a suture seat formed in the interior of the anchor member, a suture receiving slot, and at least one suture retaining structure;

the suture receiving slot being defined in the side wall, extending to the suture seat, and defining a non-linear internal passageway; and the at least one suture retaining structure being integral with the suture receiving slot and comprising at least one obstruction formed in the sidewall and created by changes in direction in the non-linear internal passageway.

18. The system of claim 17, further comprising at least one deformable barb extending from the sidewall of the anchor member.

19. The system of claim 18, having two opposed barbs, the free end of each barb extending away from the anchor member and toward the proximal end, each barb defining an angle that is between about 10° and 90° with the longitudinal axis of the anchor member.

20. The system of claim 17, wherein the suture seat and the one or more suture retaining structures are adapted to seat a suture thread along the longitudinal axis of the anchor member.

21. The system of claim 17, further comprising a suture thread having an intermediate portion and two free ends, the intermediate portion of the suture thread being engaged within the suture receiving slot, and the two free ends extending past the proximal end of the anchor member.

22. The system of claim 17, further comprising an anchor member insertion tool having a handle end and a distal end, the distal end being matable with the proximal end of the anchor member.

23. The system of claim 34, wherein the anchor member is removably pre-mated to the distal end of the insertion tool.

24. The system of claim 17, wherein the anchor member has external threads formed on at least a portion of the sidewall.

25. A system for anchoring tissue to bone, comprising:

an anchor member having a distal end, a proximal end, a sidewall disposed between the distal and proximal ends, a suture seat formed in the interior of the anchor member, a suture receiving slot defined in the side wall and extending to the suture seat, and at least one suture retaining structure integral with the suture receiving slot; and a suture thread having an intermediate portion and two free ends, the intermediate portion of the suture thread being engaged within the suture receiving slot and the two fee ends extending past the proximal end of the anchor member.

26. The system of claim 25, further comprising an anchor member insertion tool having a handle end and a distal end, the distal end being matable with the proximal end of the anchor member.

27. The system of claim 26, wherein the anchor member is removably pre-mated to the distal end of the insertion tool.

* * * * *

UNITED STATES PATENT AND TRADEMARK OFFICE
CERTIFICATE OF CORRECTION

PATENT NO. : 5,782,866
DATED : July 21, 1998
INVENTOR(S) : Richard F. Wenstrom, Jr.

It is certified that error appears in the above-indentified patent and that said Letters Patent is hereby corrected as shown below:

Column 8, Line 1 - "34" should be "22"

Signed and Sealed this

Fourth Day of May, 1999

Attest:

Q. TODD DICKINSON

Attesting Officer

Acting Commissioner of Patents and Trademarks